US007512213B2

(12) United States Patent
Zhang et al.

(10) Patent No.: US 7,512,213 B2
(45) Date of Patent: Mar. 31, 2009

(54) MULTIPLE-VIEW-ANGLE CARGO SECURITY INSPECTION METHOD AND SYSTEM

(75) Inventors: Li Zhang, Beijing (CN); Zhiqiang Chen, Beijing (CN); Kejun Kang, Beijing (CN); Haifeng Hu, Beijing (CN); Yuxiang Xing, Beijing (CN); Xinhui Duan, Beijing (CN); Yongshun Xiao, Beijing (CN); Ziran Zhao, Beijing (CN); Yuanjing Li, Beijing (CN); Yinong Liu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 11/801,250

(22) Filed: May 8, 2007

(65) Prior Publication Data
US 2008/0084962 A1    Apr. 10, 2008

(30) Foreign Application Priority Data
May 8, 2006    (CN)    ........................ 2006 1 0076574

(51) Int. Cl.
*G01N 23/04* (2006.01)
(52) U.S. Cl. .......................................... 378/57; 378/19
(58) Field of Classification Search ............... 378/4–21, 378/57, 193–197
See application file for complete search history.

(56) References Cited

U.S. PATENT DOCUMENTS 5,604,778 A    2/1997    Polacin et al. ................. 378/9
5,878,103 A    3/1999    Sauer et al. .................... 378/15
6,584,170 B2    6/2003    Aust et al. ..................... 378/57
2004/0109532 A1    6/2004    Ford et al. .................... 378/57
2005/0276376 A1*    12/2005    Eilbert ......................... 378/57
2008/0084962 A1*    4/2008    Zhang et al. ................. 378/57

FOREIGN PATENT DOCUMENTS

| CN | 1392405 A | 1/2003 |
| GB | 2 192 120 A | 12/1987 |
| GB | 2 203 620 A | 10/1988 |

OTHER PUBLICATIONS

International Search Report in PCT/CN2007/001432, Jul. 26, 2007 (English Translation) 4 pages.

* cited by examiner

*Primary Examiner*—Courtney Thomas
(74) *Attorney, Agent, or Firm*—Kenyon & Kenyon LLP

(57) ABSTRACT

A multiple-view-angle cargo security inspection method for inspecting an object using a cargo security inspection system, the cargo security inspection system including a radiation source for generating a beam of rays for transmitting through the object to be inspected and a data collecting unit for collecting the transmission projection data after the beam of rays has transmitted through the inspected object, the method including a scanning step including: rotating the radiation source and/or the object about a rotation axis so as to achieve a relative rotation, thereby positioning the radiation source in a plurality of discrete positions with different view angles with respect to the inspected object, wherein, in each view angle, the radiation source moves along a straight line in a direction parallel to the rotation axis and at the same time scans the inspected object so as to acquire the transmission projection data at each view angle.

17 Claims, 3 Drawing Sheets

MULTIPLE-VIEW-ANGLE CARGO SECURITY INSPECTION METHOD AND SYSTEM

FIELD OF THE INVENTION

The present invention relates to the technical field of radiation detection, in particular, to a multiple-view-angle cargo security inspection method.

BACKGROUND INFORMATION

Security inspection is of great importance in fields such as anti-terrorism and fighting against trafficking in drugs and smuggling. After terrorist attacks of the United States on Sep. 11, 2001, countries of the whole world attach more and more importance to security inspection on civil aviation. At the same time, the requirements on the security inspection of various cargo become higher and higher with the in-depth development of fighting against trafficking in drugs and smuggling. A series of security inspection measures are taken to inspect passenger's luggage and articles and cargo containers at public sites such as airports, stations, customs house and docks.

Computed tomography ("CT" for short) technology is widely used in the field of medical diagnosis and industrial nondestructive detection. The demand thereof in public security and social security increases gradually with the development of the society. Among the widely used CT scanning systems, the circular orbit scanning manner forms the majority. Such scanning manner requires a simple mechanical structure and thus is easy to realize in engineering. Besides, the corresponding reconstruction algorithm is mature and reliable. In the circular-orbit scanning system, a fan-beam CT manner or a cone-beam CT manner is usually adopted. The corresponding detectors are respectively a linear array of detectors or a plane array of detectors. The pair of an X radiation source and a detector are disposed symmetrically with respect to the rotation center of an object rotary table.

In CT scanning of objects having a large bulk using a CT scanning system, the feasible method is generally to adopt the scanning manner of rotation plus translation. That is, the object to be inspected rotates around the center axis and the radiation source detector moves simultaneously in the direction parallel to the rotation axis, thereby forming a spiral scanning trace around the object to be inspected. As to objects having a large cross section, it needs a great number of projections if a precise reconstruction is desired. This results in that the speed of the security inspection is very slow, and the efficiency is very low. Besides, a large number of data are possibly not concerned with the user. Therefore, such CT scanning system is unpractical for the airport that needs to carry out security inspection on a great number of cargoes every day due to its slower speed.

In addition, as to perspective imaging, if there are multiple articles in the direction parallel to the beam or rays, the articles overlap one another in the image. Generally, it is very hard to distinguish the articles from one another, which brings about a good many of difficulties to the inspection of contrabands.

SUMMARY OF THE INVENTION

Technical Problem to Be Solved

The object of this invention is to provide a multiple-view-angle cargo security inspection method in view of the aforesaid shortage existing in the prior art.

Technical Solution

In order to achieve the aforesaid object, the technical solution adopted in this invention is as follows:

An embodiment of the present invention provides a multiple-view-angle cargo security inspection method for inspecting an object using a cargo security inspection system, said cargo security inspection system comprising a radiation source for generating a beam of rays for transmitting through the object to be inspected and a data collecting unit for collecting the transmission projection data after the beam of rays has transmitted through the object to be inspected, said method comprising a scanning step comprising: rotating said radiation source and/or said object about a rotation axis so as to achieve a relative rotation, thereby positioning said radiation source in a plurality of discrete positions with different view angles with respect to said inspected object, wherein in each view angle, said radiation source moves along a straight line in a direction parallel to said rotation axis and at the same time scans said inspected object so as to acquire the transmission projection data at each view angle.

In one embodiment, said relative rotation is achieved by keeping said radiation source stationary and spinning the inspected object. In another embodiment, said relative rotation is achieved by keeping the inspected object stationary and rotating said radiation source around said inspected object.

Preferably, said radiation source and said data collecting unit are disposed at opposite sides of said inspected object, and in said scanning step said data collecting unit moves synchronically with the movement of said radiation source.

Preferably, said plurality of discrete positions with different view angles is a plurality of positions evenly spaced apart on a circumference.

Preferably, said plurality of discrete positions with different view angles comprises 3 to 70 positions. More preferably, said plurality of discrete positions with different view angles comprises 4 to 60 positions of view angles. Further preferably, said plurality of discrete positions with different view angles comprises 8 to 50 positions of view angles. Still further preferably, said plurality of discrete positions with different view angles comprises 10 to 40 positions of view angles. Most preferably, said plurality of discrete positions with different view angles comprises 15-25 positions of view angles.

Preferably, at two adjacent positions of view angles said radiation source moves along said straight lines in opposite directions respectively.

The method of this invention further comprises an imaging step for imaging said object to be inspected based on the transmission projection data collected by said data collecting unit.

Preferably, as far as each view angle in said imaging step is concerned, a two-dimensional perspective image of said object to be inspected at said view angle is imaged using the transmission projection data.

Preferably, said plurality of discrete positions with different view angles comprises at least three positions of view angles. Preferably, in said imaging step, a three-dimensional image of said object to be inspected is reconstructed using in combination the transmission projection data of said multiple view angles.

Preferably, said reconstruction is performed using a filter back-projection algorithm, expectation maximization algorithm or ordered subsets statistical algorithm.

Beneficial Effects of the Invention

1. Compared with the CT scanning or spiral CT scanning in the prior art, the scanning trace in the method of this invention is somewhat different. In the method of this invention, the radiation source scans a cargo with multiple parallel linear traces at different view angles with respect to said cargo so as to acquire transmission projection data at multiple view angles. Such scanning manner can be performed at a faster speed. Compared with the CT scanning or spiral CT scanning in the prior art, the transmission projection data acquired by the method of this invention are not complete as far as the three-dimensional image is concerned, but it is possible to acquire a three-dimensional image that satisfies the requirement of precision as much as possible under the condition that the requirement of speed is satisfied through proper selecting the number of view angles, thereby obtaining a balance between the scanning speed and the imaging precision.

2. The method of this invention is capable of realizing fast security inspection on a cargo (for example air containers), thereby significantly increasing the efficiency of security inspection on the cargo and thus satisfying the demand of the airport on fast security inspection on a great number of cargo.

3. Since this invention can reconstruct the three-dimensional image of a cargo, it has efficiently solved the problem that the objects overlap one another when a perspective image is reconstructed, thereby efficiently increasing the accuracy rate of inspection on articles and thus deeply facilitating inspection of contrabands.

4. The method of this invention can be realized with the present system; hence, it can realize the conventional perspective imaging and CT imaging with said system besides realizing the method of this invention, such that it is possible to carry out security inspection on the cargo in more flexible manners.

DETAILED DESCRIPTION

In order to make the technical solution provided in this invention more clear and apparent, this invention will be described hereinafter in detail with respect to embodiments by referring to the accompanying drawings.

Figure 1:
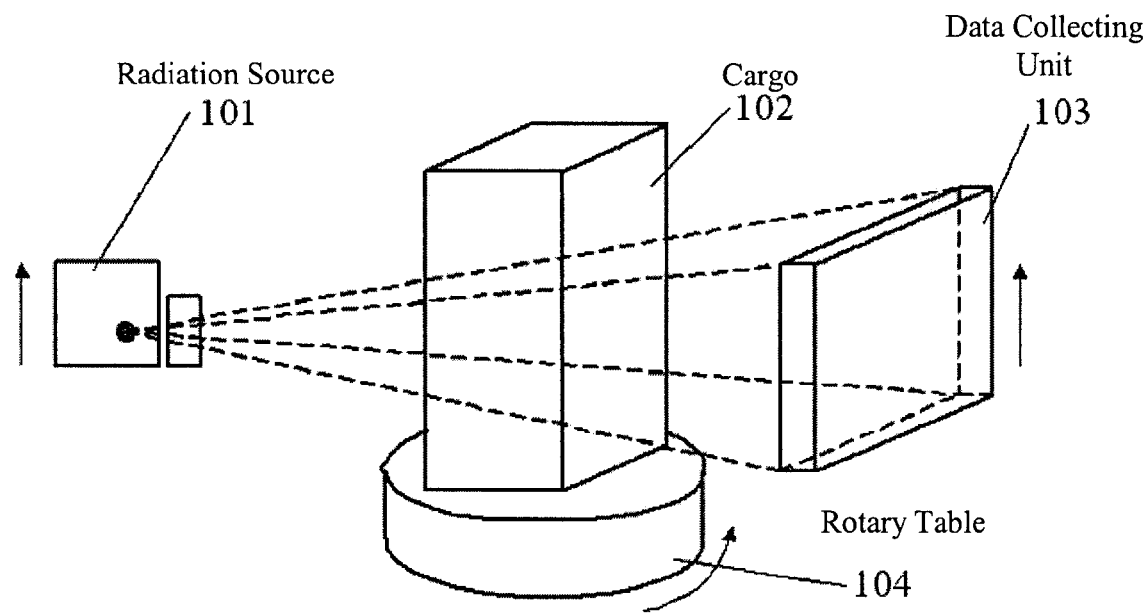
FIG. 1 is a schematic drawing of a conventional cargo security inspection system.

FIG. 1 is a schematic drawing of a conventional cargo security inspection system, which can be used to realize the method of this invention. A radiation source 101 generates a beam of X-rays or a beam of other rays for transmitting through a cargo 102. Said beam of rays transmits through the cargo 102 (in one example, said cargo 102 is an air container) carried on a rotary table 104. The transmission projection data after the beam has transmitted through the cargo are collected by a data collecting unit 103 (such as a detector array) and is transferred to a host and data processing computer (not shown). Said data collecting unit 103 is located opposite the radiation source 101. That is, said data collecting unit and said radiation source are disposed symmetrically about the center axis of the rotary table. Said host and data processing computer provides a man-machine interaction interface, and reconstructs an image of the received projection data, and displays the reconstructed image. Said rotary table 104 can drive said cargo 102 to rotate.

Said cargo inspection system usually further comprises a delivery device (see FIG. 2) for delivering the container to the rotary table and carrying the container away from the rotary table after the inspection is finished. Said cargo inspection system usually further comprises a scanning hoisting device (not shown) for carrying the radiation source and the detector and cause them to ascend and descend synchronically. Said scanning hoisting device can be two sets of hoisting platforms respectively mounted with the radiation source and the data collecting unit. In addition, the hoisting platforms can be further mounted with a horizontal collimator.

Said system can also further comprise a scanning control device for controlling the running of the radiation source, the data collecting unit and the rotary table based on the commands received from the host and data processing computer.

In order to realize fast and precise inspection, said cargo inspection system usually further comprises a device for measuring or calibrating the following system parameters: the distance D from the radiation source to the data collecting unit, the distance R from the radiation source to the rotation axis of the rotary table, the mapping position P (u, v) of the radiation source, the pixel size d of the imaging screen, and the rotation angle $\theta$ of the rotary table. The device for measuring or calibrating these system parameters is well known in the art and therefore no more details will be given herein.

Figure 2:
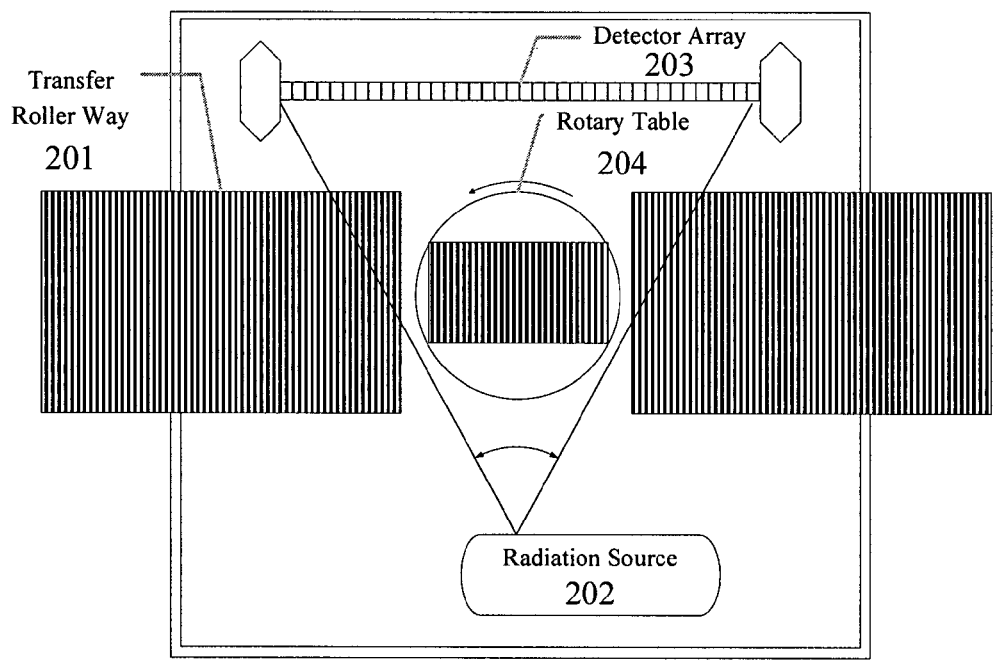
FIG. 2 is a schematic drawing of a conventional multiple-view-angle cargo inspection system with which the method of this invention may be implemented.

FIG. 2 is a schematic drawing of a multiple-view-angle cargo inspection system realizing the method of this invention. When said system works, the cargo is delivered to a rotary table 204 by a transfer roller way 201. A radiation source 202 and a detector array 203 are respectively located on two sides of the rotary table 204. The rotary table 204 can continuously rotate or be positioned at a prescribed angle. The radiation source 202 and the detector array 203 can move up and down synchronically (namely move in the direction perpendicular to the paper face of FIG. 2). When the rotary table 204 stands stationary, it is possible to acquire the transmission projection data of the air container at the present view angle by one synchronic ascending and descending of the radiation source 202 and the detector array 203.

Figure 3:
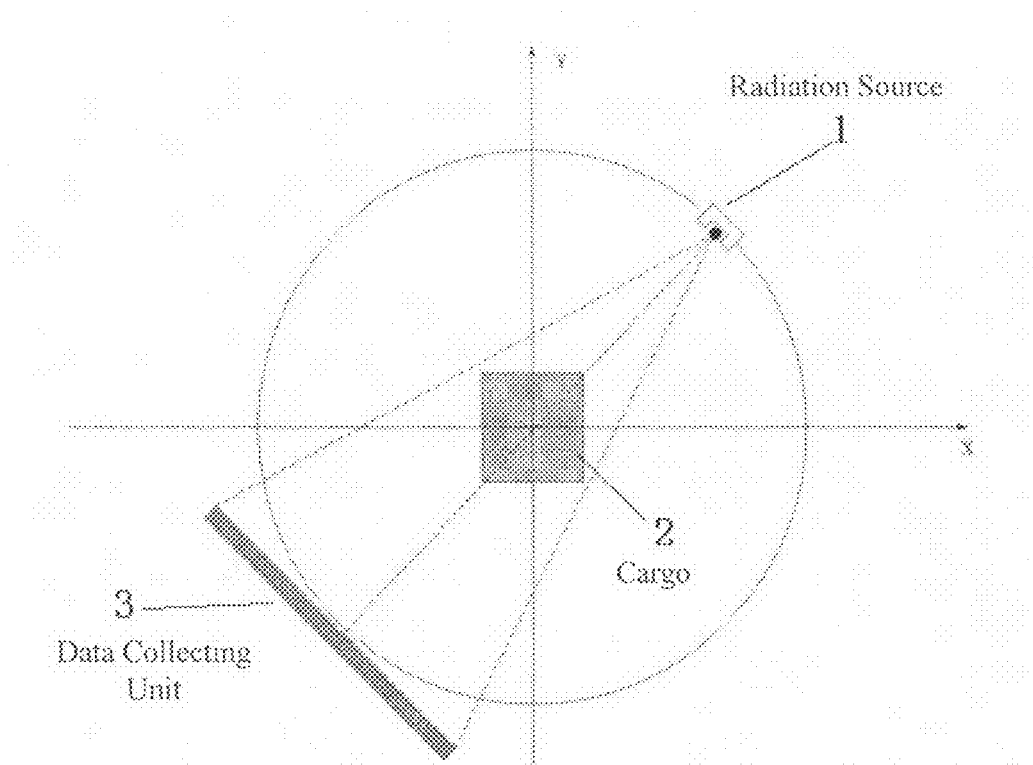
FIG. 3 is a schematic drawing of a conventional circular-trace fan-beam scanning.

The system as shown in FIG. 2 can also realize the conventional circular-trace scanning. At this moment, the radiation source 202 and the detector array 203 are kept at a fixed height, and the rotary 204 drives the cargo to rotate continuously to thereby acquire the CT projection data of the cargo at the present slice position. FIG. 3 is a schematic drawing of a conventional circular-trace fan-beam scanning. In FIG. 3, the radiation source 1 and the data collecting unit 3 are respectively disposed on two sides of the cargo 2. With respect to the cargo 2, the radiation source 1 and the data collecting unit 3 move in a circular trace.

One embodiment of the scanning process of the method of this invention is described hereinafter, comprising the following steps:

(1) initiating the system such that the radiation source and the data collecting unit make a relative rotation with respect to the cargo, and positioning said radiation source and said data collecting unit at a first view angle with respect to said cargo, wherein when said scanning process is implemented with the system as shown in FIGS. 1 and 2, said radiation source and said data collecting unit are kept stationary in the process of said relative rotation, while said cargo spins driven by the rotary table; however, it is very easy to understand that in the process of said relative rotation, it is also possible to keep said cargo stationary, while said radiation source and said data collecting unit rotate around said cargo, and at this moment said radiation source and said data collecting unit can be located near the lower end of said cargo;

(2) causing the radiation source to generate beam of rays at said first view angle to transmit through the cargo carried on said rotary table, and causing said radiation source and said data collecting unit to move upward synchronically in a linear trace and scan said cargo, wherein said linear trace is perpendicular to the plane of the relative rotation in step (1), for example, when said relative rotation is performed within a horizontal plane, said linear trace is in a vertical direction, in another word, the direction of said linear trace is parallel to the rotation axis of said relative rotation; and at the same time when the radiation source scans, said data collecting unit receives transmission projection data of the beam of rays that have transmitted through the cargo;

(3) stopping the movement of said radiation source and said data collecting unit after they move to the apex, wherein the rotary table drives the cargo to rotate an angle such that said radiation source is positioned at a second view angle different from the first view angle with respect to said cargo;

(4) causing said radiation source to generate a beam of rays at said second view angle to transmit through said cargo carried on said rotary table and move downward in a vertical direction, and the data collecting unit moves synchronically with said radiation source and receives the transmission projection data of the beam of rays that have transmitted through said cargo; and (5) repeating a process similar to the foregoing one until the rotary table carries the cargo to rotate one round such that the data collecting unit receive all projection data of the beam of rays that have transmitted through said cargo.

Figure 4:
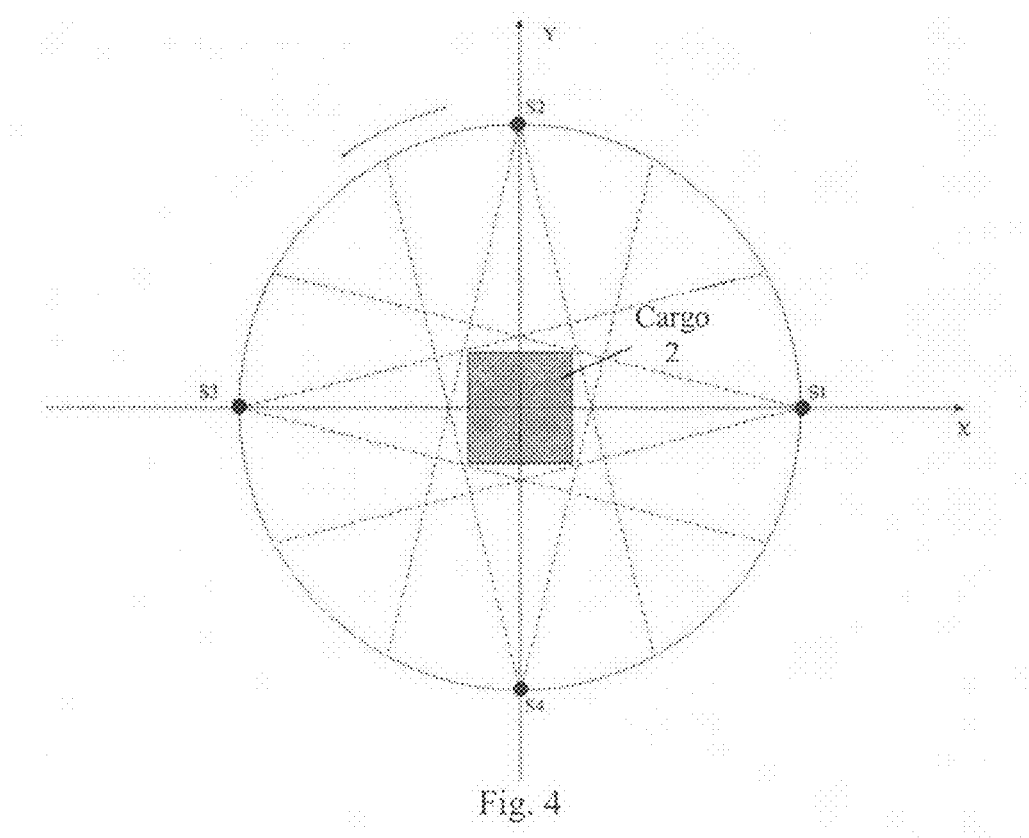
FIG. 4 is schematic drawing of a multiple-view-angle scanning manner of the multiple-view-angle cargo inspection system provided in this invention.

FIG. 4 shows a relative positional relationship between the radiation source and the cargo in one embodiment. In FIG. 4, the radiation source is located in four different positions of view angles S1, S2, S3 and S4 with respect to the cargo 2. Each position of view angle corresponds to one linear scanning as stated above. In the method of this invention, multiple positions of view angles can be multiple positions evenly spaced apart on a circumference, as shown in FIG. 4. The number of these positions of view angles can be selected according to the requirements of the desired scanning speed and imaging precision. This is easy for those ordinarily skilled in the art to do. For example, said multiple discrete positions of view angles can comprise 3 to 70 positions of view angles. In order to further increase the scanning speed, said multiple discrete positions of view angles can comprise 4 to 60 positions of view angles. In order to still further increase the scanning speed, said multiple discrete positions of view angles can comprise 8 to 50 positions of view angles. In order to even further increase the scanning speed, said multiple discrete positions of view angles can comprise 10 to 40 positions of view angles. Preferably, said multiple discrete positions of view angles can comprise 15 to 25 positions of view angles. When said multiple positions of view angles are evenly spaced apart on a circumference, it is very easy to determine the angle of each relative rotation according to the determined number of the positions of view angles. For example, when the number of the positions of view angles is 24, the rotary table drives the cargo to rotate 15 degrees each time.

Based on the transmission projection data acquired in the aforesaid scanning process, the host and data processing computer can reconstruct these projection data into an image and display it. In this invention, as far as each view angle during imaging is concerned, it is possible to use the transmission projection data at said view angle to image a two-dimensional image of said cargo at said view angle, or to use in combination the transmission projection data of said multiple view angles to reconstruct a three-dimensional image of said cargo. Of course, it is possible to acquire the two-dimensional perspective image of said cargo as well as the three-dimensional perspective image of said cargo at each view angle. When the three-dimensional image is reconstructed, it preferably needs transmission projection data acquired at least three positions of view angles.

Said reconstruction of three-dimensional image can be performed by a filtered-backprojection algorithm ("FBP" for short), expectation maximum algorithm ("EM" for short), or ordered subset EM ("OSEM" for short).

When reconstructing the received projection data of multiple view angles into an image by FBP, the reconstructing process comprises the following steps:

(1) filtering the received projection data of multiple view angles, the specific process of which is as follows: suppose $F^p(\rho,\theta)$ is a one-dimensional fourier transform of the received projection data of the multiple view angles in a direction parallel to the receiving plane of the data collecting unit, filter processing the received projection data of the multiple view angles according to the formula $$M_\theta(t) = \int_{-\infty}^{+\infty} F^p(\rho, \theta)|\rho|e^{2\pi j\rho t} d\rho$$

to acquire the filter processed result of the projection data of the multiple view angles, wherein $\rho$ and $\theta$ are respectively the radial coordinate and the angular coordinate; and (2) back projecting the filter processed projection data of the multiple view angles, the specific process of which is as follows: suppose $\tilde{f}(x,y)$ is the reconstructed image, back-projection processing the filter processed result according to the formula $$M_\theta(t) = \int_{-\infty}^{+\infty} F^p(\rho, \theta)|\rho|e^{2\pi j\rho t} d\rho$$

to acquire the reconstructed image of the projection data of the multiple view angles, wherein x and y are respectively the horizontal ordinate and the longitudinal coordinate.

When reconstructing the projection data of the multiple view angles into an image by EM, the reconstructing process comprises the following two steps, namely E-step: calculating expectation value of the conditional likelihood function; and M-step: calculating the maximum of the anticipation function.

The EM process will be described in details hereinafter with a specific example:
(1) suppose x is the reconstructed image, $a_{ij}$ is a projection matrix coefficient, and initialization m=0,$\hat{x}^m$ is positive;
(2) perform the following steps until converging:
   a) $x^1=\hat{x}^m$, m=m+1;
   b) calculating the projection value, wherein $$\mu_t^i = \sum_{j=1}^{J} a_{tj} x_j^i, \ t \in S_i;$$

c) back projecting the projection value, wherein $$x_j^{i+1} = x_j^i \sum_{t \in S_i} \frac{y_t a_{tj}}{\mu_t^j} \Big/ \sum_{t \in S_i} a_{tj},$$

$$j = 1, 2, \ldots, J; \text{ and}$$

d) acquiring $\hat{x}^m$=x'.

The OSEM is similar to the EM, but the convergence rate thereof is higher than that of the EM, and the imaging quality thereof is close to that of the EM. This invention can also adopt the OSEM. When the received projection data of the multiple view angles are reconstructed into an image by the OSEM, the reconstructing process comprises the following steps:
(1) suppose x is the reconstructed image, $a_{ij}$ is a projection matrix coefficient, and initialization m=0,$\hat{x}^m$ is positive;
(2) performing the following steps until converging:
   a) $x^1=\hat{x}^m$, m=m+1;
   b) calculating the projection value as to each subset i=1, 2, . . . , n, wherein $$\mu_t^i = \sum_{j=1}^{J} a_{tj} x_j^i, \ t \in S_i,$$

and performing back projection of the projection value, wherein $$x_j^{i+1} = x_j^i \sum_{t \in S_i} \frac{y_t a_{tj}}{\mu_t^j} \Big/ \sum_{t \in S_i} a_{tj},$$

$$j = 1, 2, \ldots, J; \text{ and}$$

c) acquiring $\hat{x}^m$=x'.

Figure 5A:
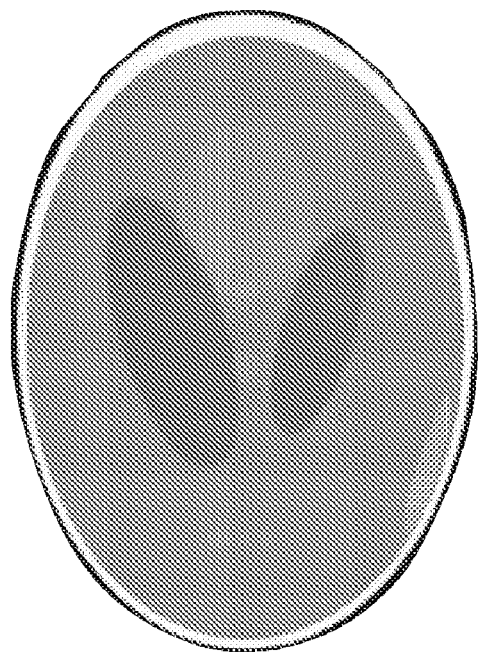
FIGS. 5a and 5b are simulation results of the Shepp-Logn head model.
Figure 5B:
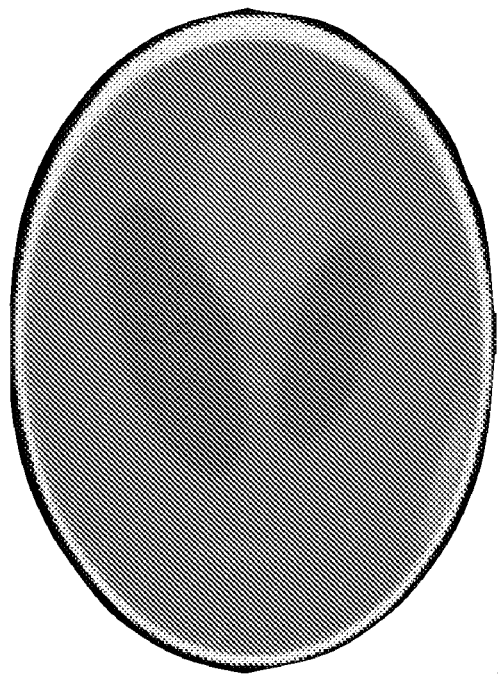

After completing image reconstruction of the received projection value of the multiple view angles, the host and data processing computer displays the reconstructed image. For detailed result of reconstructed image, see FIG. 5. FIGS. 5*a* and 5*b* are results of simulation of Shepp-Logn head model.

In addition, the system that realizes this invention can also realize dual-view angle scanning mode and CT slice scanning mode.

In the dual-view angle scanning mode, the system only acquires a two-dimensional perspective image at two orthogonal view angles and display on the computer screen two perspective views simultaneously for the operator to determine. Said mode has a short scanning time and a high pass rate. However, the determining manner and basis of operator, similar to the present inspection system, need higher experiences and responsibility.

In the CT slice scanning mode, the system first acquires the CT projection data of the prescribed slice position of an air container, then generates a corresponding CT image of said position through data reconstruction and provides an alarm. Since said slice image can reflect the magnitude and distribution manner of the density information of the cargo in the corresponding section, the accuracy of alarm is greatly increased, but the scanning time is longer.

In the multiple-view-angle scanning mode of this invention, the system acquires continuously a plurality of two-dimensional perspective images at different view angles, approximately reconstructs the data of the triaxiality of the whole object by reconstruction with incomplete data, and displays them on the computer screen for the operator to determine. Besides, interactive operation can be performed on the related projection data via a man-machine interface, and at the same time the key suspicious regions are displayed with prominence. In this mode, the system can preliminarily realize giving an alarm as to dangerous articles, such as explosives. Besides, the scanning time is moderate. Therefore, this mode serves as the preferred scanning manner of this invention.

The system can switch among these three scanning modes automatically and does not need any switching time. Therefore, different scanning modes can be used flexibly in the process of actual application according to the requirement of the risk assessment of the air container or the security level of the airport. Under the condition of seeking pass rate, the dual-view angle scanning mode is selected; and in usual circumstance, the multiple-view-angle scanning mode is first used, and then CT slice scanning is performed according to the circumstances on the specific position of the suspicious air container that cannot be cleared during determination of the data of the triaxiality.

What is claimed is:

1. A multiple-view-angle cargo security inspection method for inspecting an object using a cargo security inspection system, said cargo security inspection system comprising a radiation source for generating a beam of rays for transmitting through the object and a data collecting unit for collecting transmission projection data after the beam of rays has transmitted through the object, said method comprising:
   in a scanning step:
      rotating at least one of the radiation source and the object about a rotation axis so as to achieve a relative rotation, thereby positioning the radiation source in a plurality of discrete positions with different view angles with respect to the object; and
      for each view angle:
         interrupting the relative rotation; and
         during the interruption of the relative rotation, simultaneously (a) moving the radiation source along a respective straight line in a direction parallel to the rotation axis and (b) scanning the object by the radiation source, so as to acquire the transmission projection data at each view angle.

2. The method of claim 1, wherein the relative rotation is achieved by keeping the radiation source stationary and spinning the object.

3. The method of claim 1, wherein the relative rotation is achieved by keeping the object stationary and rotating the radiation source around the object.

4. The method of claim 1, wherein:
   the radiation source and the data collecting unit are disposed at opposite sides of the object; and in the scanning step, the data collecting unit moves synchronically with the movement of the radiation source.

5. The method of claim 1, wherein the plurality of discrete positions with different view angles are evenly spaced apart from each other on a circumference.

6. The method of claim 1, wherein the plurality of discrete positions with different view angles comprises 3 to 70 positions of view angles.

7. The method of claim 6, wherein the plurality of discrete positions with different view angles comprises 4 to 60 positions of view angles.

8. The method of claim 7, wherein the plurality of discrete positions with different view angles comprises 8 to 50 positions of view angles.

9. The method of claim 8, wherein the plurality of discrete positions with different view angles comprises 10 to 40 positions of view angles.

10. The method of claim 9, wherein the plurality of discrete positions with different view angles comprises 15 to 25 positions of view angles.

11. The method of claim 1, wherein at two adjacent positions of view angles, the radiation source moves along the respective straight lines in opposite directions respectively.

12. The method of claim 1, further comprising:
   in an imaging step, imaging the object based on the transmission projection data collected by the data collecting unit.

13. The method of claim 12, wherein, in the imaging step, for each view angle, the object is imaged as a two-dimensional perspective image using the transmission projection data of the respective view angle.

14. The method of claim 12, wherein the plurality of discrete positions with different view angles comprises at least three positions of view angles.

15. The method of claim 12, wherein, in the imaging step, a three-dimensional image of the object is constructed using in combination the transmission projection data of multiple ones of the view angles.

16. The method of claim 15, wherein the construction is performed using one of a filter back-projection algorithm, expectation maximization algorithm, and ordered subsets statistical algorithm.

17. A multiple-view-angle cargo security inspection system, comprising:
   a radiation source for generating a beam of rays for transmitting through an object being inspected;
   a data collecting unit for collecting transmission projection data after the beam of rays has been transmitted through the object;
   a rotation arrangement configured to rotate at least one of the radiation source and the object about a rotation axis so as to achieve a relative rotation, the radiation source thereby being positioned in a plurality of discrete positions with different view angles with respect to the object; and
   a scanning arrangement configured to, for each view angle, so as to acquire the transmission projection data at each view angle:
      interrupt the relative rotation; and
      during the interruption of the relative rotation, simultaneously (a) move the radiation source along a respective straight line in a direction parallel to the rotation axis and (b) cause the radiation source to scan the object.

* * * * *